(12) United States Patent
Thompson

(10) Patent No.: US 12,083,238 B1
(45) Date of Patent: Sep. 10, 2024

(54) AUTOMATIC SOLUTION INJECTION APPARATUS AND METHOD

(71) Applicant: Gabriel Lee Thompson, Pensacola, FL (US)

(72) Inventor: Gabriel Lee Thompson, Pensacola, FL (US)

(*) Notice: Subject to any disclaimer, the term of this patent is extended or adjusted under 35 U.S.C. 154(b) by 688 days.

(21) Appl. No.: 17/236,148

(22) Filed: Apr. 21, 2021

Related U.S. Application Data

(60) Provisional application No. 63/024,554, filed on May 14, 2020.

(51) Int. Cl.
| | |
|---|---|
| *A61L 2/18* | (2006.01) |
| *A61L 2/24* | (2006.01) |
| *F24F 11/38* | (2018.01) |
| *F24F 11/88* | (2018.01) |
| *F24F 13/22* | (2006.01) |

(52) U.S. Cl.
CPC .............. *A61L 2/186* (2013.01); *A61L 2/24* (2013.01); *F24F 11/38* (2018.01); *F24F 11/88* (2018.01); *F24F 13/222* (2013.01); *A61L 2202/14* (2013.01); *A61L 2202/15* (2013.01)

(58) Field of Classification Search
CPC ..................................................... A61L 2/186
See application file for complete search history.

(56) References Cited

U.S. PATENT DOCUMENTS

| | | | | | |
|---|---|---|---|---|---|
| 3,954,974 | A | * | 5/1976 | Herzog | A61K 33/40 424/616 |
| 2006/0265106 | A1 | * | 11/2006 | Giles | A01B 79/005 700/283 |
| 2009/0224907 | A1 | * | 9/2009 | Sinha | G08B 21/245 340/541 |
| 2015/0266657 | A1 | * | 9/2015 | Corney | B65D 81/245 222/478 |
| 2018/0129177 | A1 | * | 5/2018 | Coin | F04D 13/06 |

* cited by examiner

*Primary Examiner* — Kevin Joyner
(74) *Attorney, Agent, or Firm* — J. Nevin Shaffer, Jr.

(57) ABSTRACT

An automatic solution injection apparatus and method with a motor where the motor operates an action arm. A container configured to retain fluid and where the container is sealed with a fluid check valve and where the fluid check valve is connected with the motor action arm such that operation of the motor action arm opens the fluid check valve such that fluid exits the container. A printed circuit board (PCB) controller connected with the motor where the PCB controller automatically controls the operation of the motor and a pump connected with the motor such that operation of the motor actuates the pump where the pump directs fluid that exits the container to a dispenser nozzle.

20 Claims, 5 Drawing Sheets

AUTOMATIC SOLUTION INJECTION APPARATUS AND METHOD

CROSS REFERENCE TO RELATED APPLICATION

This application claims the benefit of previously filed U.S. provisional patent application No. 63/024,554 filed Apr. 27, 2020 for a DrainBot Automatic HVAC Solution Injector. The Applicant hereby claims the benefit of this provisional application under 35 U.S.C. § 119. The entire content of this provisional application is incorporated herein by this reference.

FIELD OF THE INVENTION

This invention relates to an automatic solution injection device. In particular, in accordance with one embodiment, the invention relates to an automatic solution injection apparatus and method with a motor where the motor operates an action arm. A container is provided that is configured to retain fluid and the container is sealed with a fluid check valve. The fluid check valve is connected with the motor action arm such that operation of the motor action arm opens the fluid check valve such that fluid exits the container. A printed circuit board (PCB) controller is connected with the motor where the PCB controller automatically controls the operation of the motor and a pump is connected with the motor such that operation of the motor actuates the pump where the pump directs fluid that exits the container to a dispenser nozzle.

BACKGROUND OF THE INVENTION

Many types of equipment generate fluid that must be drained in order for the equipment to operate as designed. Heating, Ventilation and Air Conditioning (HVAC) equipment, by way of example only and not by limitation, generates significant amounts of condensation/fluid, particularly in summer months, that is sent to drain lines that deposit the fluid away from the equipment, usually outside of the structure. These drain lines however develop mold and bacteria on the inside of the drain line that clogs and blocks the drain line. The blockage causes fluid to back up and, if unattended to, to overflow the drain line. When this happens fluid overflows inside the structure causing extensive damage to the structure in cases where the blockage is not detected early enough.

The state of the art requires the HVAC operator, homeowner, for example, to schedule periodic times to manually flush the drain line or add chlorine bleach to it to remove the mold and bacteria. Even though this can help it does not usually remove all the mold and bacteria when done intermittently because mold and bacteria, once established, regenerate rapidly.

Thus, there is a need in the art for a system to clean mold and bacteria from drain lines and, once clean, to provide treatment regularly so that mold and bacteria are prevented from regenerating after treatment.

It therefore is an object of this invention to provide an apparatus and method to treat drain lines, particularly HVAC drain lines, periodically and automatically with bacteria and mold killing fluid.

It is a further object of the invention to provide an automatic solution injection system that is easy to operate and economical to install and maintain.

SUMMARY OF THE INVENTION

Accordingly, the automatic solution injection apparatus and method of the present invention, according to one embodiment, includes a motor where the motor operates an action arm. A container is provided that is configured to retain fluid and the container is sealed with a fluid check valve. The fluid check valve is connected with the motor action arm such that operation of the motor action arm opens the fluid check valve such that fluid exits the container. A printed circuit board (PCB) controller is connected with the motor where the PCB controller automatically controls the operation of the motor and a pump is connected with the motor such that operation of the motor actuates the pump where the pump directs fluid that exits the container to a dispenser nozzle.

All terms used herein are given their common meaning so that "motor" identifies and describes a mechanical device for operating other devices, such as an "action arm" and a "pump", as are known in the art.

"Fluid check valve" describes a device that mechanically blocks passage of fluid when in a closed position and which allows fluid to pass when in an open position.

"PCB controller" describes a programable computing device as is known in the art which controls the timing, speed, duration, and general operation of attached devices such as motors, pumps, and alarms. Further the PCB controller processes data obtained from attached devices and identifies operational status of the attached devices as normal or out of normal.

According to another aspect, the invention further includes a one way air valve through which fluid from the container passes before exiting the dispenser nozzle, the one way air valve operating to prevent fluid from moving back to the container when the motor is not in operation.

In one aspect, the PCB controller includes a sensor for measuring fluid flow according to power required to operate the motor and the pump.

In one aspect, a low fluid warning alarm is activated when increased power is required to operate the motor and the pump. In another aspect, the low fluid warning alarm is visual and in one aspect, the low fluid warning alarm is audible.

In another aspect, the invention includes a status indicator where the status indicator provides a visual indication of the status of the operation of the apparatus. In one aspect, the visual indication is green when the PCB controller detects the apparatus is functioning normally and the visual indication is red when the PCB controller detects an apparatus misfunction.

In one aspect, the fluid in the container is a solution consisting of a combination of hydrogen peroxide, water and oil.

According to another embodiment, an automatic solution injection apparatus consists of an enclosure with an outside and an inside. A motor on the inside of enclosure operates an action arm. A container is connected with the enclosure where the container is configured to retain fluid and where the container is sealed with a fluid check valve and where the fluid check valve is connected with the motor action arm such that operation of the motor action arm opens the fluid check valve such that fluid exits the container. A printed circuit board (PCB) controller is located on the inside of the enclosure and is connected with the motor where the PCB controller automatically controls the operation of the motor. A pump is located on the inside of the enclosure and is connected with the motor such that operation of the motor actuates the pump where the pump directs fluid that exits the container to a dispenser nozzle. An activation switch on the outside of the enclosure is connected with the PCB controller for activation of the PCB controller and a status indicator on the outside of the enclosure is connected with the PCB controller where the status indicator provides a visual indication of the status of the operation of the apparatus. A power source is connected with the enclosure and with the PCB controller, the motor and the pump.

In one aspect, the invention further includes a one way air valve through which fluid from the container passes before exiting the dispenser nozzle, the one way air valve operating to prevent fluid from moving back to the container when the motor is not in operation.

In one aspect, the PCB controller includes a sensor for measuring fluid flow according to power required to operate the motor and the pump. In another aspect, a low fluid warning alarm is activated when increased power is required to operate the motor and the pump. In another aspect, the low fluid warning alarm consists of a visual warning and an audible warning.

In one aspect, the visual indication is green when the PCB controller detects the apparatus is functioning normally and the visual indication is red when the PCB controller detects an apparatus misfunction.

In another aspect, the fluid in the container is a solution consisting of a combination of hydrogen peroxide, water and oil. In one aspect, the solution consists of a combination that is approximately sixty percent hydrogen peroxide, thirty five percent water and five percent essential oils.

According to another embodiment, an automatic solution injection method consists of:

a. providing an enclosure with an outside and an inside; a motor on the inside of the enclosure where the motor operates an action arm; a container connected with the enclosure where the container is configured to retain fluid and where the container is sealed with a fluid check valve and where the fluid check valve is connected with the motor action arm such that operation of the motor action arm opens the fluid check valve such that fluid exits the container; a printed circuit board (PCB) controller on the inside of the enclosure connected with the motor where the PCB controller automatically controls the operation of the motor; a pump on the inside of the enclosure connected with the motor such that operation of the motor actuates the pump where the pump directs fluid that exits the container to a dispenser nozzle; an activation switch on the outside of the enclosure connected with the PCB controller for activation of the PCB controller; a status indicator on the outside of the enclosure connected with the PCB controller where the status indicator provides a visual indication of the status of the operation of the apparatus; and a power source connected with the enclosure and with the PCB controller, the motor and the pump; and b. connecting the dispenser nozzle with a drain line.

In one aspect, the fluid in the container is a solution consisting of a combination of hydrogen peroxide, water and oil.

In one aspect, the drain line is a HVAC drain line.

In another aspect, the method further includes an activation switch on the outside of the enclosure connected with the PCB controller for activation of the PCB controller such that the PCB controller operates according to a user selected program to automatically inject fluid into the drain line periodically at selected times.

DESCRIPTION OF THE DRAWINGS

Other objects, features and advantages of the present invention will become more fully apparent from the following detailed description of the preferred embodiment, the appended claims and the accompanying drawings in which:

DETAILED DESCRIPTION OF THE INVENTION

Figure 1:
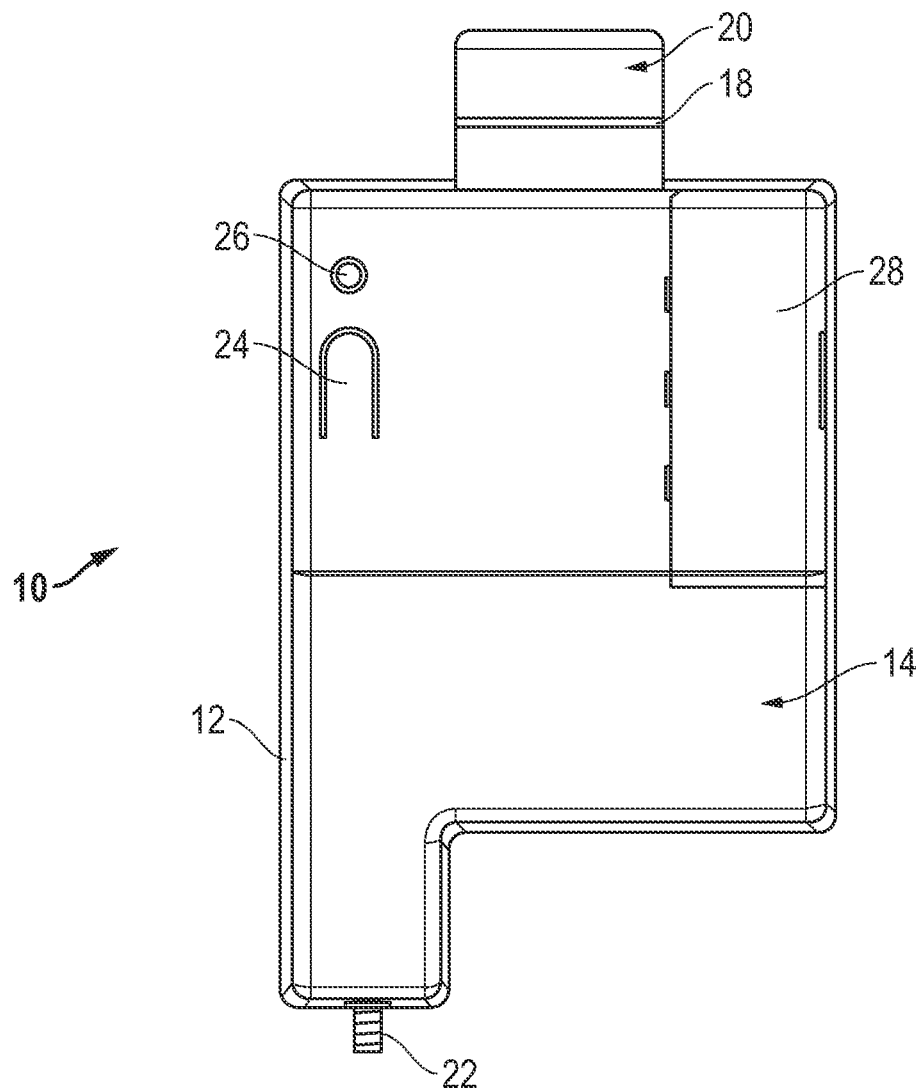
FIG. 1 is a front view of the automatic fluid injection apparatus showing the outside of the enclosure with a container attached.

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the invention be regarded as including equivalent constructions to those described herein insofar as they do not depart from the spirit and scope of the present invention.

For example, the specific sequence of the described process may be altered so that certain processes are conducted in parallel or independent, with other processes, to the extent that the processes are not dependent upon each other. Thus, the specific order of steps described herein is not to be considered implying a specific sequence of steps to perform the process. In alternative embodiments, one or more process steps may be implemented by a user assisted process and/or manually. Other alterations or modifications of the above processes are also contemplated.

In addition, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

It should also be noted that a plurality of hardware and software devices, as well as a plurality of different structural components, may be utilized to implement the invention. Furthermore, and as described in subsequent paragraphs, the specific configurations illustrated in the drawings are intended to exemplify embodiments of the invention and that other alternative configurations are possible.

A preferred embodiment of the present invention is illustrated by way of example in FIGS. 1-5. With specific reference to FIGS. 1 and 2, automatic solution injection apparatus and method 10 includes an enclosure 12 with an outside 14 and an inside 16. Enclosure 12 is configured as shown to enclose and retain the elements of the invention as more fully described hereafter and as shown in the figures. Enclosure 12 is preferably comprised of sturdy material, plastic, metal or the like.

Enclosure 12 is configured to receive and removably retain container 18. Container 18 is configured to hold fluid 20, not shown for clarity, which, as will be described more fully hereafter, when released from container 18 exits enclosure 12 at dispenser nozzle 22.

FIG. 1 shows activation switch 24 and status indicator 26 on the outside 14 of enclosure 12 as will be described more fully hereafter. Also shown is battery compartment cover 28.

Figure 2:
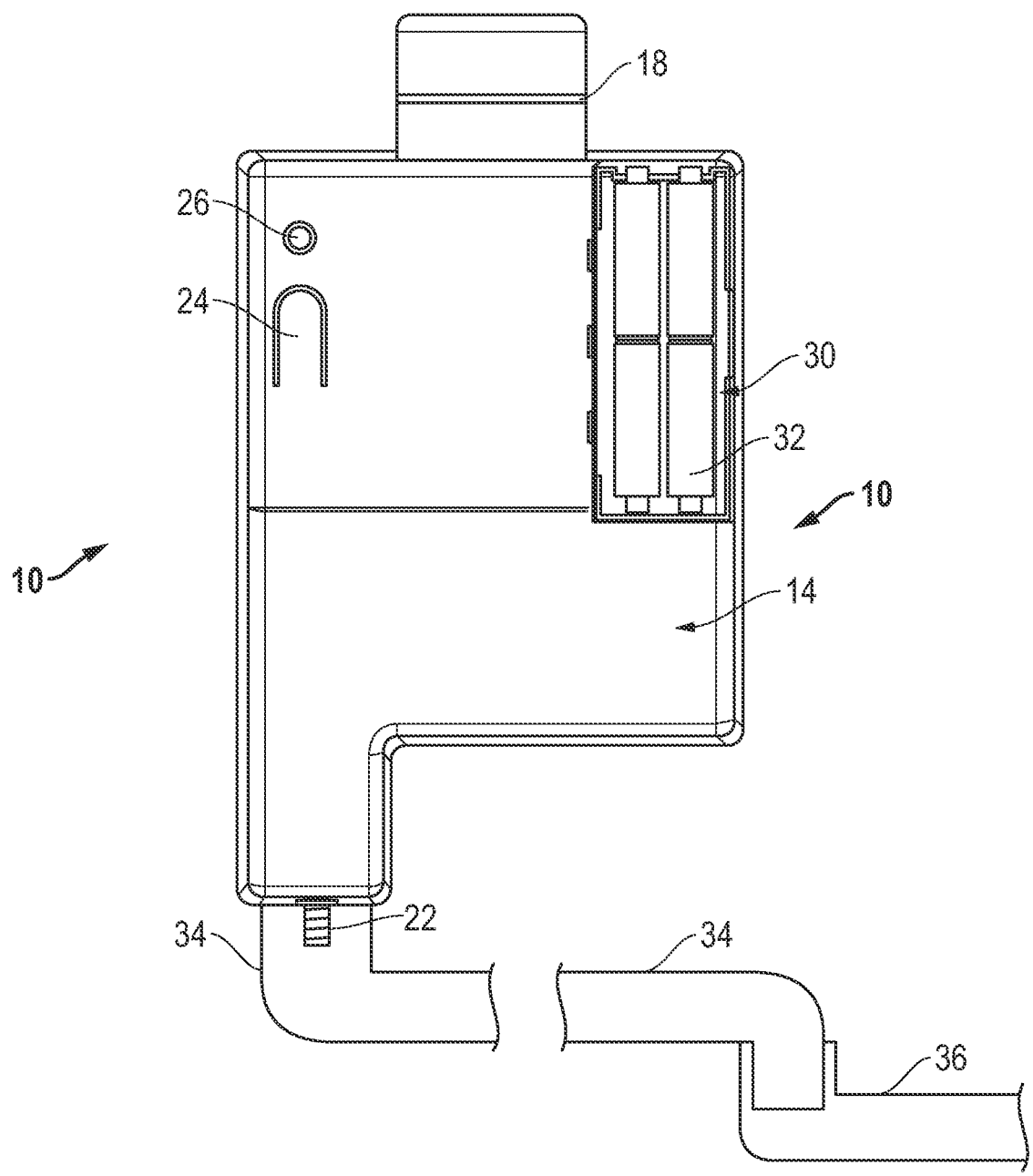
FIG. 2 is a front partial cut away view of the invention of FIG. 1 showing the outside of the enclosure, a cut away view of the batteries in the enclosure and a connection tube connecting the dispenser nozzle with a drain line.

Referring to FIG. 2, battery compartment cover 28 is removed to show power source 30, preferably batteries 32. Any power source 30 is included within the scope of the invention such as with connection to an electrical outlet, wired or wireless or the like.

FIG. 2 also shows dispenser nozzle 22 connected by connector 34, such as a plastic, PVC, or metal tube for example only and not by limitation, to a drain line 36 such as an HVAC condensation drain line, for example only and not by limitation.

Figure 3:
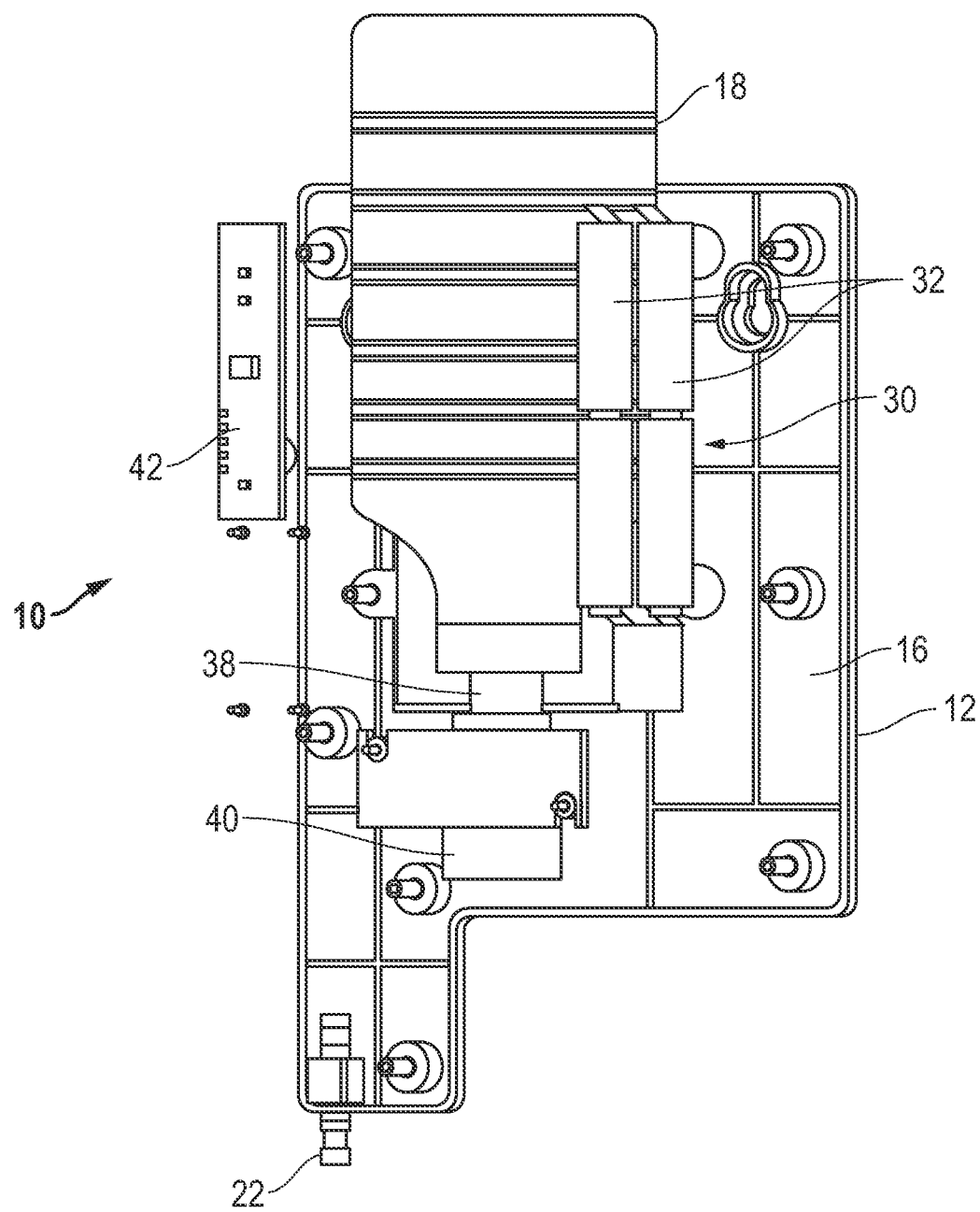
FIG. 3 is a front partial cut away view of the invention of FIG. 1 showing the back of the PCB controller and the batteries of FIG. 2.

FIG. 3 is a cut away front view showing the inside of the enclosure 12 with power source 30, batteries 32, and the container 18 in place and removably connected with motor 38. Also shown are pump 40 and PCB controller 42.

Figure 4:
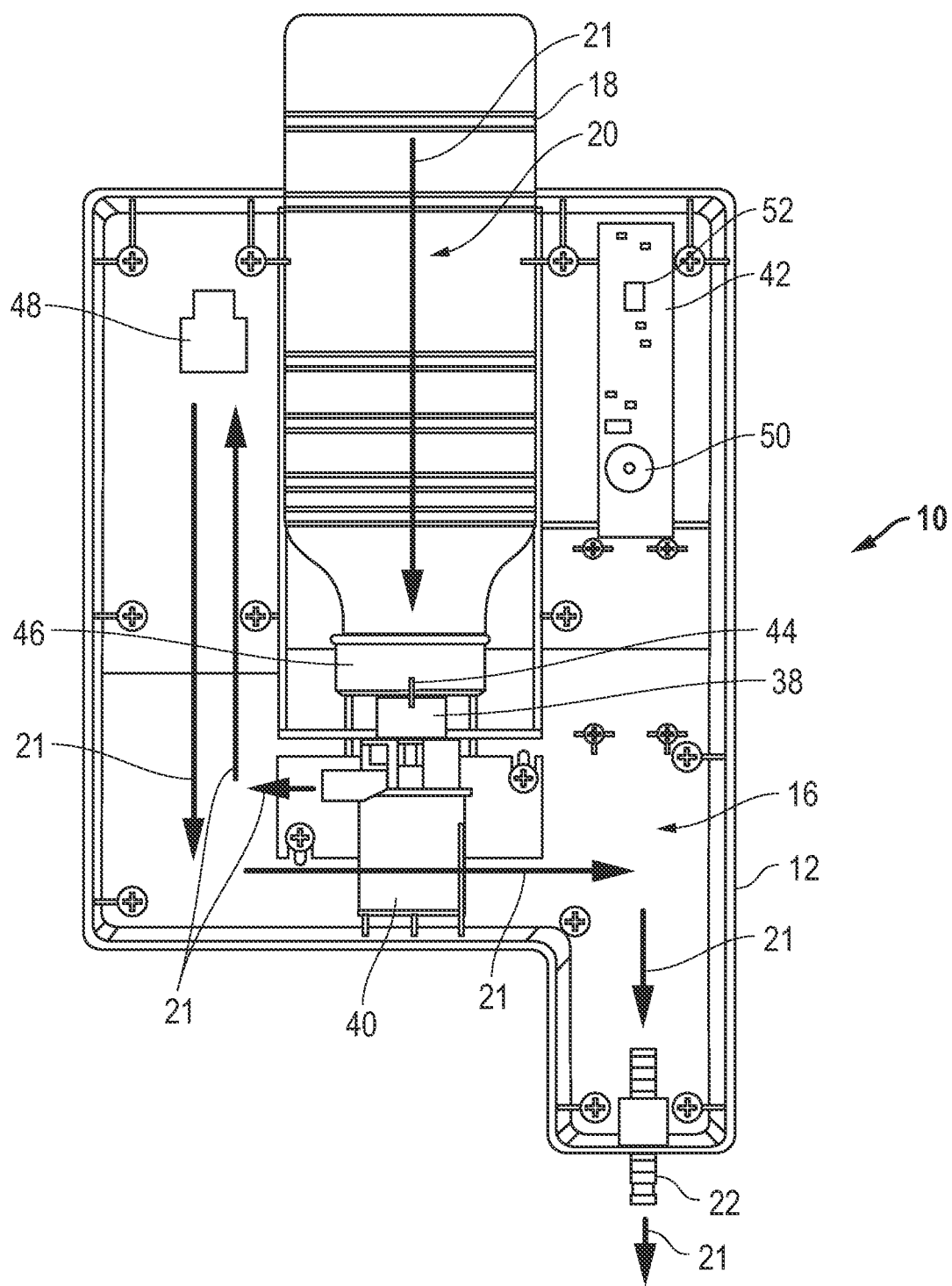
FIG. 4 is a back cut away view of the invention of FIG. 1.

Referring now to FIG. 4, the elements and operation of automatic solution injection apparatus 10 are shown to include motor 38 with an action arm 44. Container 18 includes fluid check valve 46 connected at motor 38 such that operation of the action arm 44 interacts with fluid check valve 46 to release fluid 20. Fluid check valve 46 is spring loaded shut so that fluid in the container 18 is prevented from leaving unless and until container 18 is placed in contact with action arm 44.

The flow of fluid 20 is shown by the direction arrows 21 such that fluid 20 flows from container 28, when action arm 44 opens fluid check valve 46, to pump 40 where it is pumped to dispenser nozzle 22. Preferably, fluid 20 is directed past a one way air valve 48 such that one way air valve 48 prevents fluid 20 from flowing back to container 18 when motor 38 is not in operation.

Figure 5:
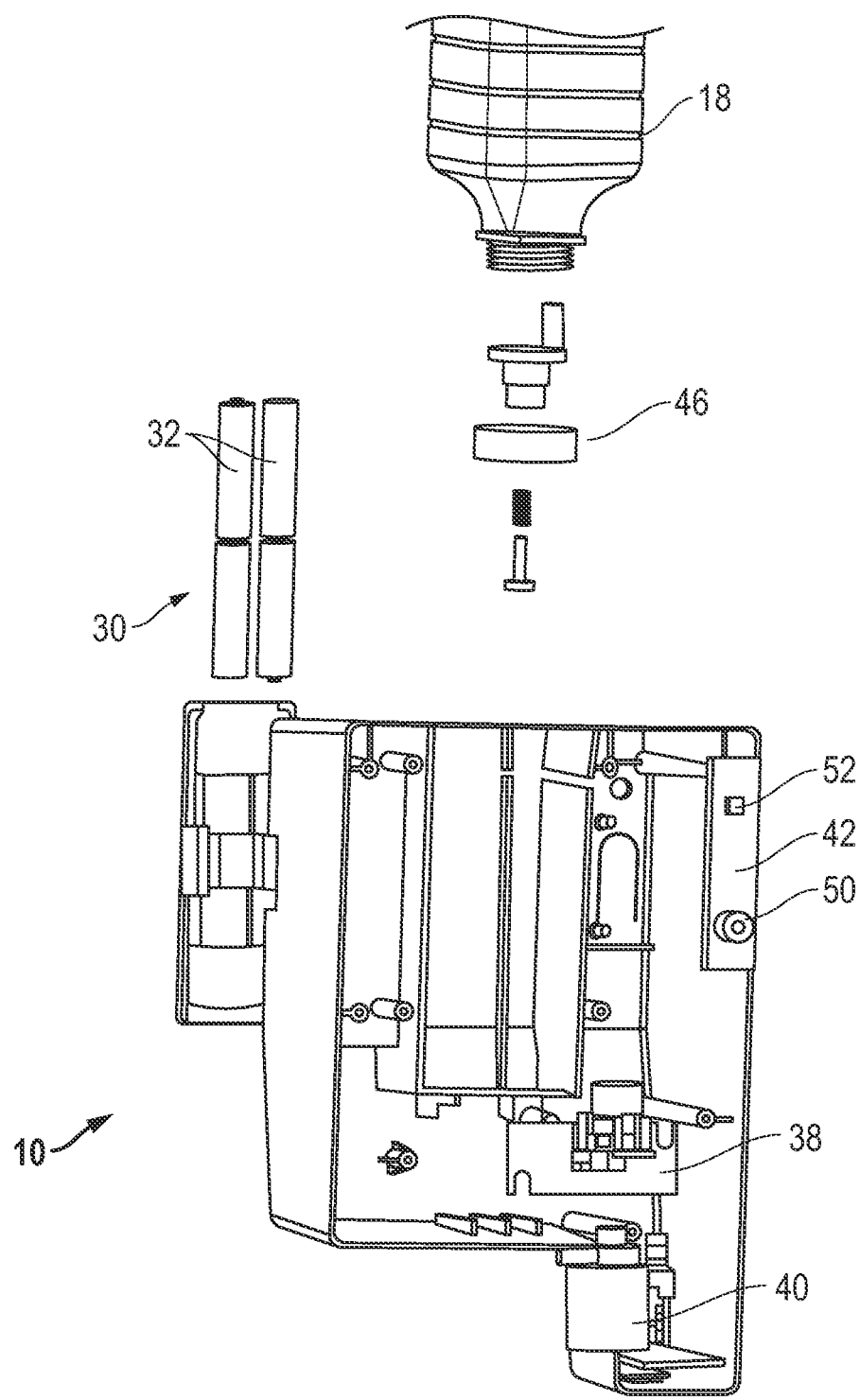
FIG. 5 is a back cut away, partial exploded, view of the invention of FIG. 1 showing the container check valve.

FIG. 4 also shows audio alarm 50 connected with PCB controller 42 and FIG. 5 shows an exploded view of the spring actuated fluid check valve 46, power source 30, batteries 32, and motor 38 and pump 40.

By way of further description, in one aspect, the PCB controller 42 includes a sensor 52 for measuring fluid flow according to power required to operate the motor 38 and the pump 40. In another aspect, a low fluid warning alarm 54, status indicator 26, is activated when sensor 53 determines that increased power is required to operate the motor 38 and the pump 40. In another aspect, the low fluid warning alarm 54 consists of a visual warning, where status indicator 26 is an LED light, for example only. In another aspect the low fluid warning alarm 54 is an audible warning as with audio alarm 50, a buzzer for example only.

In one aspect, the status indicator 26 provides a visual indication that is green when the PCB controller 42 detects the apparatus 20 is functioning normally and the visual indicator 26 is red when the PCB controller 42 detects an apparatus misfunction.

In another aspect, the fluid 20 in the container 18 is a solution consisting of a combination of hydrogen peroxide, water and oil. In one aspect, the Applicant has found it preferable that the fluid 20 solution consists of a combination that is approximately sixty-percent hydrogen peroxide, thirty-five-percent water and five-percent essential oils.

In another aspect, the automatic solution injection apparatus and method 10 further includes an activation switch 24 on the outside 14 of the enclosure 12 connected with the PCB controller 42 for activation of the PCB controller 42 such that the PCB controller 42 operates according to a user selected program to automatically inject fluid 20 into the drain line 36 periodically at selected times. That is, for example only, the activation switch 24 may be pressed once to schedule fluid 20 to be injected every day, twice for every two days, three times for every three days, or any desired schedule deemed appropriate to the user.

The description of the present embodiments of the invention has been for purposes of illustration, but is not intended to be exhaustive or to limit the invention to the form disclosed. Many modifications and variations will be apparent to those of ordinary skill in the art. As such, while the present invention has been disclosed in connection with an embodiment thereof, it should be understood that other embodiments may fall within the spirit and scope of the invention as defined by the following claims.

What is claimed is:

1. An automatic solution injection apparatus comprising:
   a. a motor wherein the motor operates an action arm;
   b. a container wherein the container is configured to retain fluid and wherein the container is sealed with a fluid check valve and wherein the fluid check valve is connected with said action arm such that operation of the action arm opens the fluid check valve such that fluid exits said container;
   c. a printed circuit board (PCB) controller connected with said motor wherein the PCB controller automatically controls the operation of the motor wherein the PCB controller includes a sensor for measuring fluid flow according to power required to operate the motor and a pump and wherein a low fluid warning alarm is activated when increased power is required to operate the motor and the pump; and
   d. the pump connected with the motor such that operation of the motor actuates the pump wherein the pump directs fluid that exits said container to a dispenser nozzle.

2. The apparatus of claim 1 further including a one way air valve through which fluid from the container passes before exiting the dispenser nozzle, the one way air valve operating to prevent fluid from moving back to the container when the motor is not in operation.

3. The apparatus of claim 1 wherein the low fluid warning alarm is visual.

4. The apparatus of claim 1 wherein the low fluid warning alarm is audible.

5. The apparatus of claim 1 further including a status indicator wherein the status indicator provides a visual indication of the status of the operation of the apparatus.

6. The apparatus of claim 5 wherein the visual indication is green when the PCB controller detects the apparatus is functioning normally and wherein the visual indication is red when the PCB controller detects an apparatus misfunction.

7. The apparatus of claim 1 wherein in the fluid in the container is a solution consisting of a combination of hydrogen peroxide, water and oil.

8. The apparatus of claim 7 wherein the solution consists of a combination that is approximately sixty percent hydrogen peroxide, thirty five percent water and five percent essential oils.

9. An automatic solution injection apparatus comprising:
a. an enclosure with an outside and an inside;
b. a motor on the inside of said enclosure wherein the motor operates an action arm;
c. a container connected with the enclosure wherein the container is configured to retain fluid and wherein the container is sealed with a fluid check valve and wherein the fluid check valve is connected with said action arm such that operation of the action arm opens the fluid check valve such that fluid exits said container;
d. a printed circuit board (PCB) controller on the inside of the enclosure connected with said motor wherein the PCB controller automatically controls the operation of the motor wherein the PCB controller includes a sensor for measuring fluid flow according to power required to operate the motor and a pump wherein a low fluid warning alarm is activated when increased power is required to operate the motor and the pump and wherein the low fluid warning alarm consists of a visual warning and an audible warning;
e. the pump located on the inside of the enclosure connected with the motor such that operation of the motor actuates the pump wherein the pump directs fluid that exits said container to a dispenser nozzle;
f. un activation switch on the outside of the enclosure connected with the PCB controller for activation of said PCB controller;
g. a status indicator on the outside of the enclosure connected with the PCB controller wherein the status indicator provides a visual indication of the status of the operation of the apparatus; and
h. a power source connected with the enclosure and with the PCB controller, the motor and the pump.

10. The apparatus of claim 9 further including a one way air valve through which fluid from the container passes before exiting the dispenser nozzle, the one way air valve operating to prevent fluid from moving back to the container when the motor is not in operation.

11. The apparatus of claim 9 wherein the visual indication is green when the PCB controller detects the apparatus is functioning normally and wherein the visual indication is red when the PCB controller detects an apparatus misfunction.

12. The apparatus of claim 9 wherein the fluid in the container is a solution consisting of a combination of hydrogen peroxide, water and oil.

13. The apparatus of claim 12 wherein the solution consists of a combination that is approximately sixty percent hydrogen peroxide, thirty five percent water and five percent essential oils.

14. An automatic HVAC solution injection method comprising:
a. providing a motor wherein the motor operates an action arm; a container wherein the container is configured to retain fluid and wherein the container is sealed with a fluid check valve and wherein the fluid check valve is connected with said action arm such that operation of the action arm opens the fluid check valve such that fluid exits said container; a printed circuit board (PCB) controller connected with said motor wherein the PCB controller automatically controls the operation of the motor wherein the PCB controller includes a sensor for measuring fluid flow according to power required to operate the motor and a pump and wherein a low fluid warning alarm is activated when increased power is required to operate the motor and the pump, the pump connected with the motor such that operation of the motor actuates the pump wherein the pump directs fluid that exits said container to a dispenser nozzle; and
b. connecting the dispenser nozzle with a drain line.

15. The method of claim 14 wherein the drain line is a HVAC drain line.

16. The method of claim 14 further including an activation switch on the outside of the enclosure connected with the PCB controller for activation of said PCB controller such that the PCB controller operates according to a user selected program to automatically inject fluid into the drain line periodically al selected times.

17. The method of claim 14 further including a one way air valve through which fluid from the container passes before exiting the dispenser nozzle, the one way air valve operating to prevent fluid from moving back to the container when the motor is not in operation.

18. The method of claim 14 wherein the low fluid warning alarm is selected from a group of alarms consisting of: visual and audible.

19. The method of claim 14 further including a status indicator wherein the status indicator provides a visual indication of the status of the operation of the apparatus.

20. The method of claim 19 wherein the visual indication is green when the PCB controller detects the apparatus is functioning normally and wherein the visual indication is red when the PCB controller detects an apparatus misfunction.

* * * * *